US012396781B2

United States Patent
Chen et al.

(10) Patent No.: US 12,396,781 B2
(45) Date of Patent: Aug. 26, 2025

(54) ELECTROSURGICAL PENCIL INTEGRATING MODULE AND AN ELECTROSURGICAL DEVICE POSSESSING MODULE THEREOF

(71) Applicant: Taipei Medical University, Taipei (TW)

(72) Inventors: Huan Chieh Chen, Taipei (TW); Tien Jen Lin, Taipei (TW)

(73) Assignee: Taipei Medical University, Taipei (TW)

( * ) Notice: Subject to any disclaimer, the term of this patent is extended or adjusted under 35 U.S.C. 154(b) by 357 days.

(21) Appl. No.: 18/206,339

(22) Filed: Jun. 6, 2023

(65) Prior Publication Data
US 2024/0407828 A1 Dec. 12, 2024

(51) Int. Cl.
*A61B 18/14* (2006.01)
*A61B 18/00* (2006.01)

(52) U.S. Cl.
CPC .... *A61B 18/14* (2013.01); *A61B 2018/00595* (2013.01); *A61B 2018/1412* (2013.01); *A61B 2218/008* (2013.01)

(58) Field of Classification Search
CPC .......... A61B 18/14; A61B 2018/00595; A61B 2018/1412; A61B 2218/007; A61B 2218/008
(Continued)

(56) References Cited

U.S. PATENT DOCUMENTS 5,085,657 A * 2/1992 Ben-Simhon ........... A61M 1/85
606/49
5,460,602 A * 10/1995 Shapira ............... A61B 18/1402
604/35
(Continued)

FOREIGN PATENT DOCUMENTS

WO WO-2005046498 A1 * 5/2005 ......... A61B 18/1402
WO WO-2017031245 A1 * 2/2017 ......... A61B 18/1402

*Primary Examiner* — Beverly M Flanagan
(74) *Attorney, Agent, or Firm* — James W. Huffman; Huffman Law Group, PC

(57) ABSTRACT

Embodiments of the present disclosure are directed to an electrosurgical pencil integrating module and an electrosurgical device possessing module thereof. The electrosurgical device includes an electrosurgical pencil and an integrating module. The electrosurgical pencil includes a working section. A distal end of the working section is a blade portion. The neck portion extends from the adjacent insulating layer of the working section toward the blade portion. The integrating module is used to combine with the electrosurgical pencil. The integrating module further includes an elastic securing tube and a conduit. The elastic securing tube is used for docking and accommodating the working section. The inner diameter of the inlet end of the elastic securing tube is larger than the maximal cross section of the working section. After the working section passes through the elastic securing tube, the position of the neck portion is hold by the internal wall of the elastic securing tube. In addition, the inner portion of the conduit and the inner portion of the elastic securing tube are interconnected. When the neck portion of the working section is secured, the blade portion of the working section is just protruded outside the integrating module. By fixing the integrating module on the neck portion, which has a small diameter and a predetermined size, of the working section, the purpose of reducing the volume of the integrating module and being universally (Continued)

applicable to electrosurgical pencils of different brands can be achieved.

18 Claims, 4 Drawing Sheets

(58) Field of Classification Search
USPC .......................................................... 606/45
See application file for complete search history.

(56) References Cited

U.S. PATENT DOCUMENTS

| | | | |
|---|---|---|---|
| 7,731,716 B1* | 6/2010 | Christoudias | A61B 18/1482 |
| | | | 606/49 |
| 2016/0114088 A1* | 4/2016 | Minskoff | A61M 1/804 |
| | | | 604/541 |
| 2017/0325886 A1* | 11/2017 | Graham | A61B 18/1206 |
| 2022/0117646 A1* | 4/2022 | Kleyman | A61M 1/76 |

\* cited by examiner

ELECTROSURGICAL PENCIL INTEGRATING MODULE AND AN ELECTROSURGICAL DEVICE POSSESSING MODULE THEREOF

BACKGROUND OF THE INVENTION

1. Field of the Present Disclosure

The present disclosure relates to an electrosurgical pencil device, more particularly, to an electrosurgical pencil integrating module which is applied to insulate the electrode of the electrosurgical pencil and has both smoke and fluid evacuation functions, and an electrosurgical device possessing module thereof.

2. Background

Traditionally known electrosurgical pencil produces a large amount of smoke during the process of hemostasis or tissue cutting. The principle is that when the electrode of the electrosurgical pencil contacts tissue, it generates high heat due to electric current, which carbonizes or vaporizes the tissue, resulting in surgical smoke. However, potentially harmful substances, bacteria, and viruses in surgical smoke can lead to respiratory and pulmonary diseases. In addition, surgical smoke can also irritate the eyes of medical personnel, interfere with the visibility of the surgical field of vision, and affect the outcome of surgery.

For this reason, there are many different types of electrosurgical pencils with either built-in or attached smoke-evacuating devices, which can allow doctors to remove the smoke when performing operations. Embodiments of the present disclosure are related to the following applications: U.S. patent application Ser. No. 09/729,310, "Electrosurgical pencil with a smoke evacuating blade" filed Dec. 5, 2000 (hollow electrode with holes); U.S. patent application Ser. No. 11/897,457, "Integrated smoke evacuation electrosurgical pencil and method" filed Aug. 30, 2007 (integrated, coaxial smoke suction tube, length adjustable); U.S. patent application Ser. No. 09/783,128, "Electro-surgical pencil with smoke evacuation" filed Feb. 15, 2001 (integrated, coaxial smoke suction tube, fixed length); U.S. patent application Ser. No. 08/319,265, "Electrosurgical smoke evacuator" filed Oct. 6, 1994 (attached type, coaxial smoke suction tube, fixed length), European patent application Ser. No. 07122453.9, "Length adjustable electro-surgical pencil with suction means" filed Nov. 12, 2004 (integrated, smoke suction tube above, length adjustable); Chinese patent application Ser. No. 201110459659.X, "Adjustable electrotome smoke-absorbing device for surgical operation" filed Dec. 31, 2011 (integrated, coaxial smoke suction tube, length adjustable); Chinese patent application Ser. No. 201120574280.9, "Surgery electric knife attached type smoke absorbing device" filed Dec. 31, 2011 (attached type, smoke suction tube below, fixed length), and other patent applications are all design patents for different types of electrosurgical devices with smoke evacuation. All of these applications are incorporated by reference herein in their entirety.

The design of smoke evacuation devices has the following directions, such as the U.S. patent application Ser. No. 09/729,310 filed Dec. 5, 2000, which focuses on the design of electrosurgical pencil electrodes. The device has a hollow channel in the middle of the electrosurgical pencil electrode, and a plurality of holes on both sides of the electrode communicate with it. The smoke generated during electric burning will be sucked into the hollow channel through the holes and then discharged. However, the design of this special electrode is a disposable product for single use, with high manufacturing costs. If repeated disinfection is used, the holes and the hollow channels in its design are not easy to clean, which increases the risk of infection. At the same time, it is also difficult to cover and insulate the external surface of the electrosurgical electrode.

Another design method is to integrate the electrosurgical pencil and the smoke evacuation device, such as the European patent application Ser. No. 07122453.9 filed Nov. 12, 2004, which focuses on not only the body, but also the front and rear positions of the smoke suction tube can be adjusted. However, the disadvantages of this design include complex design, high cost, and increased volume of the electrosurgical pencil, as well as the fact that the smoke suction tube is located above the electrosurgical electrode, which can block the surgeon's vision. Especially during minimally invasive surgery, the smoke suction tube can obscure the electrosurgical electrode and the lesion. If the smoke suction tube is moved backward, the smoke evacuating function will be less effective. In addition, for example, the U.S. patent application Ser. No. 11/897,457 filed Aug. 30, 2007, and the Chinese patent application Ser. No. 201120574280.9 filed Dec. 31, 2011, are also designs that integrate an electrosurgical pencil and a smoke evacuation device. The focus of these patent applications is to place the electrosurgical electrode within the lumen of the smoke suction tube (coaxial), and the smoke suction tube can be moved forward or backward. Although the suction tubes with coaxial design have better smoke evacuating performance than the non-coaxial (electrode placed outside the lumen of the smoke suction tube) ones, their common disadvantages include complex structure, high cost, and bulky. Moreover, due to its design that the smoke suction tube is movable and encloses the whole electrode, the diameter of the smoke suction tube must be relatively wide. If the tip of the smoke suction tube is too close to a distal end of the electrode, it will still obscure the surgeon's field of vision, which is unfavorable for performing minimally invasive surgery.

Another design is to use an independent smoke evacuation device attached to the electrosurgical pencil, with the common advantages of simple structure and low cost. For example, the design of the U.S. patent application Ser. No. 08/319,265 filed Oct. 6, 1994, is to fit a smoke evacuation device onto the front end of the electrosurgical pencil. The disadvantage is that the position of the tip of the smoke suction tube relative to the electrode may vary due to the use of different brands or forms of electrosurgical pencils, which affects the smoke evacuation effect. Moreover, due to the large diameter of the smoke suction tube, it is not possible to reach the distal end of the electrode, otherwise, it may obscure the surgeon's field of vision. The design of Chinese patent application Ser. No. 201120574280.9 filed Dec. 31, 2011, is to attach a smoke evacuation device to the neck of the electrosurgical electrode through a C-shaped flexible clamp. The advantage is that the tip of the smoke suction tube can be placed closer to the distal end of the electrode, and its design is suitable for most brands or forms of electrosurgical pencils. However, the major disadvantage is its non-coaxial design (the tip of the smoke suction tube is located on the side of the electrosurgical electrode), making the smoke evacuating function less efficient, in addition, the smoke suction tube will still obscure the surgical field.

There is a special electrosurgical electrode, its external surface is coated with an insulating layer, usually made of polytetrafluoroethylene (PTFE), and only part of the distal end of the electrode is exposed. This is to avoid injury to important blood vessels or internal organs while using the electrosurgical pencil, and is beneficial for minimally invasive surgery, but will increase the manufacturing cost of the electrosurgical electrode. However, there are no specialized medical materials available on the market for the insulation of electrosurgical electrodes. Some doctors will use ordinary rubber tubes or other non-heat-resistant materials as alternative insulation for electrosurgical electrodes, but under high temperatures, it may cause combustion and cause injury to patients. The present disclosure is proposed based on the lack of the above-known technology and the protective effect of electrodes.

SUMMARY OF THE INVENTION

In response to the above shortcomings, the main purpose of the present disclosure is to provide an electrosurgical pencil integrating module and an electrosurgical device possessing module thereof. By adopting a coaxial design of a suction tube with both smoke and fluid evacuation functions, and a diameter of the suction tube is smaller, it can reach a distal end of the electrode of the electrosurgical pencil as closely as possible without obscuring the surgeon's field of vision. The effect of smoke and fluid evacuation functions is more efficient than other designs. The material is made of heat-resistant materials (such as PTFE), which also has the function of insulating the electrode of the electrosurgical pencil, as a result of being beneficial to use in narrow spaces and minimally invasive surgery. The elastic securing component with an inner diameter slightly smaller than a standard diameter of the most common electrode of the electrosurgical pencil is capable of being universally applicable to electrosurgical pencils of different brands, and the installation is easy. Therefore, the module of the present disclosure is fixed to a specific position with a smaller diameter at the distal end of the electrode of the electrosurgical pencil, which can achieve the effect of reducing the volume and weight of the device without increasing the burden of the surgeon.

In order to achieve the above purposes, one embodiment of the present disclosure is mainly directed to the electrosurgical device possessing module thereof, which comprises an electrosurgical pencil, and the electrosurgical pencil further comprises a handheld section and a working section. The handheld section is in a long cylindrical shape and is to be held by the operator during surgery. The working section is connected to the distal end of the handheld section and is mainly composed of conductive metal. The working section is also provided with an insulating layer at a proximal end of the working section and adjacent to the handheld section. The insulating layer is used to cover a portion of the conductive metal of the working section, and the distal end of the working section is provided with a blade portion. Another embodiment of the present disclosure is directed to the integrating module for assembling the electrosurgical pencil, and the integrating module further comprises an elastic securing tube and a conduit. The elastic securing tube is used for docking and accommodating the working section where the electrosurgical pencil is installed in. The elastic securing tube has an inlet end, and the inner diameter of the inlet end is larger than the maximal cross-section of the working section. The working section of the electrosurgical pencil penetrates into the elastic securing tube until the working section is clamped and locked by an elastic inner wall of the elastic securing tube. An inner portion of the elastic securing tube and an inner portion of the conduit are interconnected. The conduit is provided with a proximal relay end on the proximal end, and an internal diameter of the proximal relay end is not smaller than an internal diameter of the conduit. An axis of the elastic securing tube and an axis of the conduit extend to form an included angle greater than 0 degree and less than 20 degrees. When a neck portion of the working section is secured, the blade portion of the working section is just protruded outside the integrating module.

In order to make the above and other purposes, features, and advantages of the present disclosure more apparent and understandable, the following text provides preferred embodiments, and in conjunction with the accompanying drawings, a detailed explanation is given as follows.

BRIEF DESCRIPTION OF THE DRAWINGS

To describe the technical solutions in the embodiments of this application more clearly, the following briefly introduces the accompanying drawings required for describing the embodiments. Apparently, the accompanying drawings in the following description show merely some embodiments of this application, and a person of ordinary skill in the art may still derive other drawings from these accompanying drawings without creative efforts.

DESCRIPTION OF THE EMBODIMENTS

Figure 1:
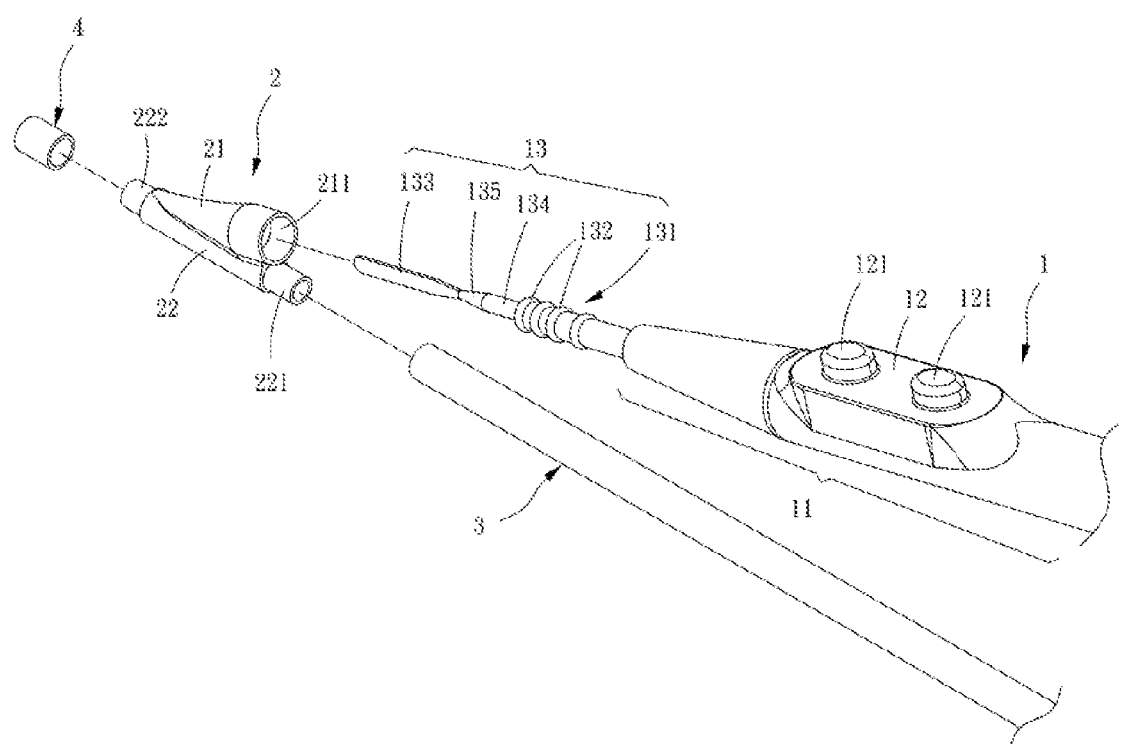
FIG. 1 is an exploded view of a three-dimensional structure according to one embodiment of the present disclosure.

Please refer to FIG. 1, which is an exploded view of a three-dimensional structure according to one embodiment of the present disclosure. As shown in FIG. 1, one embodiment of the present disclosure is directed to an electrosurgical pencil integrating module, which mainly comprises an electrosurgical pencil 1, an integrating module 2, and a suction pipe 3. The electrosurgical pencil 1 has a long cylindrical handheld section 11 for holding the electrosurgical pencil 1. In this embodiment, the handheld section 11 is provided with an operation panel 12, and the operation panel 12 is provided with a plurality of operation buttons 121, which are used to control the different functions of the electrosurgical pencil 1. At a distal end of the handheld section 11, a working section 13 is connected, which is mainly composed of conductive metal. At a proximal end of the working section 13, which is adjacent to the handheld section 11, is an insulating layer 131. The insulating layer 131 is used to cover a portion of the conductive metal of the working section 13. In this embodiment, an outer surface of the insulating layer 131 has a plurality of outwardly protruding annular bodies 132. At a distal end of the working section 13 is a blade portion 133, which is flat and used for electrocautery during surgery. A neck portion 134 extends from the insulating layer 131 of the working section 13 towards the blade portion 133. The neck portion 134 is cylindrical, and a cone portion 135 is disposed between the neck portion 134 and the blade portion 133. The cone portion 135 is conical. In this embodiment, the cone portion 135, the neck portion 134, and the blade portion 133 are formed integrally.

Figure 2:
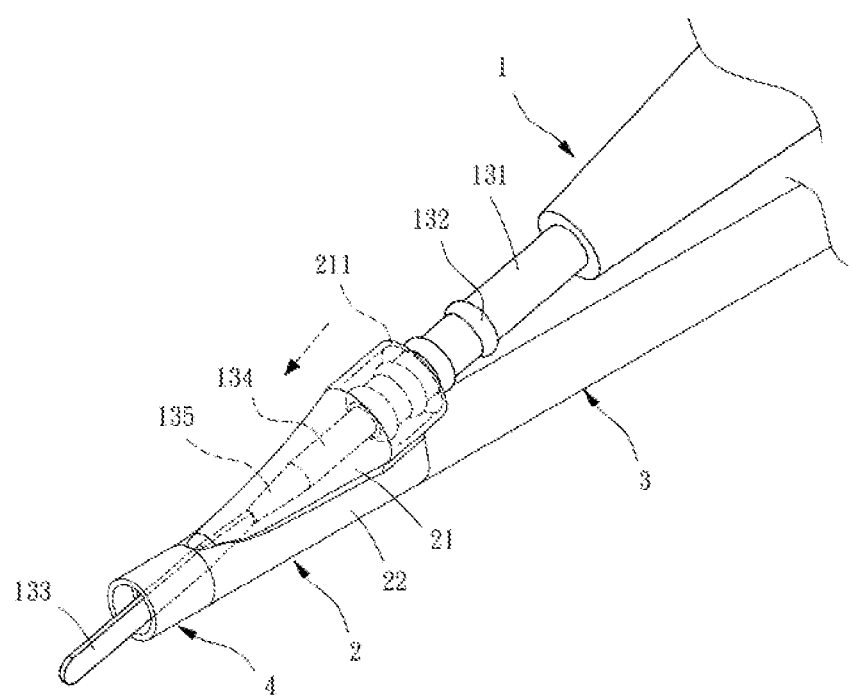
FIG. 2 is a three-dimensional combination diagram according to one embodiment of the present disclosure.
Figure 3:
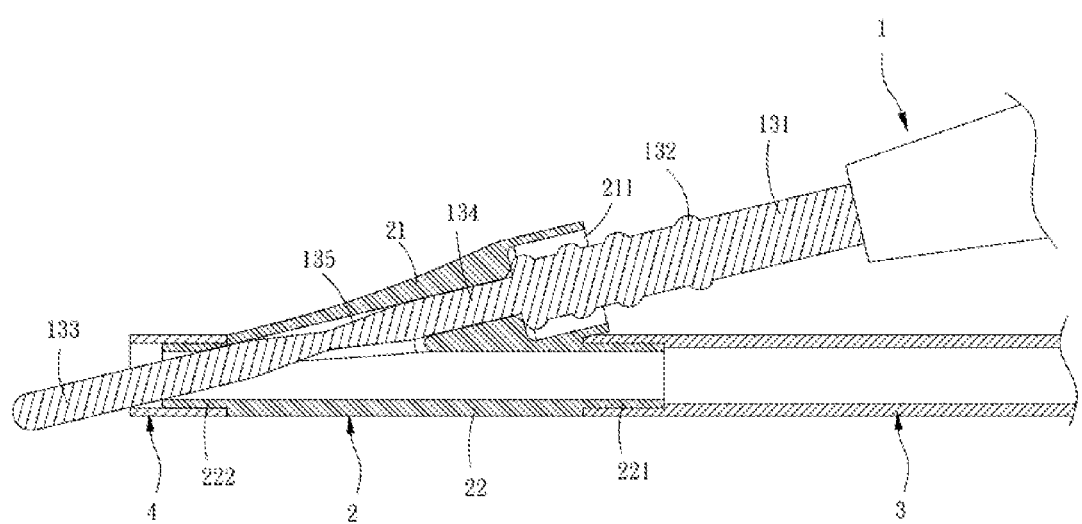
FIG. 3 is a combined sectional view according to one embodiment of the present disclosure.

Please refer to FIG. 1 continuously. The integrating module 2 is used for assembling the electrosurgical pencil 1 and the suction pipe 3. The integrating module 2 is provided with an elastic securing tube 21 and a conduit 22. An axis of the elastic securing tube 21 and an axis of the conduit 22 extend to form an included angle greater than 0 degree and less than 20 degrees, resulting in an inclined shape of the elastic securing tube 21 when the conduit 22 is placed horizontally. An inner portion of the elastic securing tube 21 and an inner portion of the conduit 22 are interconnected. In this embodiment, the elastic securing tube 21 and the conduit 22 are integrally formed. The elastic securing tube 21 is used for docking and accommodating the working section 13 of the electrosurgical pencil. The elastic securing tube 21 has an inlet end 211, and a diameter of the inlet end 211 is larger than a maximal cross-section of the working section 13, facilitating the working section 13 to penetrate the elastic securing tube 21, as shown in FIG. 2, which is a three-dimensional combination diagram according to one embodiment of the present disclosure. Until the working section 13 is clamped and locked by an elastic inner wall of the elastic securing tube 21, as shown in FIG. 3, which is a combined sectional view according to one embodiment of the present disclosure, the blade portion 133 of the working section 13 is just protruded outside the integrating module 2. Ideally, an exposed length of the blade portion 133 of the working section 13 is between 1 mm and 5 mm.

Figure 4:
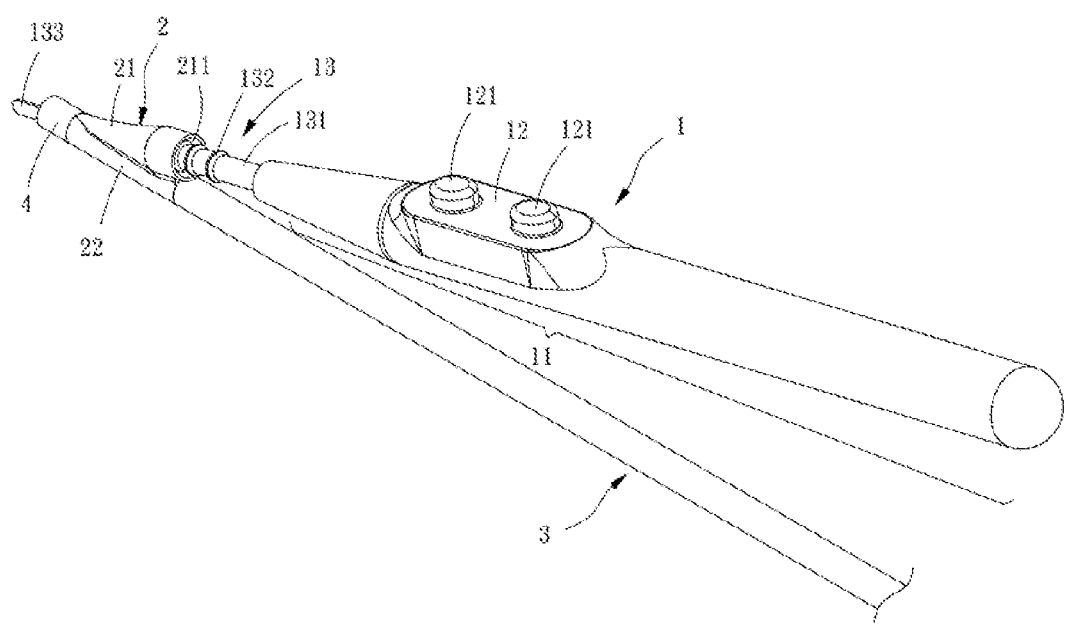
FIG. 4 is a combined completion diagram according to one embodiment of the present disclosure.

Please refer to FIG. 1 continuously. The conduit 22 of the integrating module 2 is used to interconnect with the suction pipe 3, and a position of the suction pipe 3 is on the same side as the electrosurgical pencil 1. The conduit 22 is provided with a proximal relay end 221 on the proximal end corresponding to the suction pipe 3, and an internal diameter of the proximal relay end 221 is not smaller than an internal diameter of the conduit 22. As a result, when the proximal relay end 221 and the suction pipe 3 are interconnected with each other, an outer wall of the proximal relay end 221 is precisely embedded with the inner tube wall of the suction pipe 3, to form a continuous channel. The conduit 22 also has a distal relay end 222 located at a distal end of the conduit 22 where the blade portion 133 protrudes. The internal diameter of the distal relay end 222 is not larger than the internal diameter of the conduit 22, and the distal relay end 222 is correspondingly interconnected with an insulating pipe 4 that is cylindrical and composed of electric and heat insulating material, and the insulating pipe 4 may be used to adjust the exposed length of the blade portion 133. The length of the insulating pipe 4 may be cut according to the user's need, so that the exposed length of the blade portion 133 is between 1 mm and 5 mm, as shown in FIG. 4, which is a combined completion diagram according to one embodiment of the present disclosure.

The inner diameter of the elastic securing tube 21 is slightly smaller than the diameter of the neck portion 134. By mounting the integrating module 2 with the electrosurgical pencil 1 and the suction pipe 3, the integrating module 2 is secured with the electrode at the neck portion 134 of the working section 13 using elastic force. While the diameter of the neck portion 134 is standardized (2.36~2.40 mm), the integrating module 2 can be connected universally to different brands of electrosurgical pencils. In addition to insulating the electrode of the electrosurgical pencil 1, the integrating module 2 has the functions of both smoke and fluid evacuation. The insulating pipe sleeve 4, which has the function of electric and heat insulation, can be placed as close as possible to the source of smoke without obscuring the surgical field. It can be flexibly used in narrow spaces and effectively protect surrounding tissues from burns.

However, the above-described implementation method is a preferred implementation example, and when it is not possible to limit the scope of implementation of the present disclosure, any equivalent changes or modifications made by the scope of the patent application for the present disclosure and the content of the specification should fall within the scope of the following patents for the present disclosure.

What is claimed is:

1. An electrosurgical integrating module used to connect an electrosurgical pencil and a suction pipe, wherein the electrosurgical pencil has a working section, which is mainly made of conductive metal, a blade portion is disposed at a distal end of the working section, which is used for electrocautery, and the electrosurgical pencil integrating module comprises:

an elastic securing tube, which is used for docking and accommodating the working section where the electrosurgical pencil is installed, the elastic securing tube has an inlet end, and an internal diameter of the inlet end is larger than a maximal cross-section of the working section; and a conduit, which is used for docking with the suction pipe, an axis of the elastic securing tube and an axis of the conduit extend to form an included angle greater than 0 degree and less than 20 degrees, and an inner portion of the elastic securing tube and an inner portion of the conduit are interconnected, the conduit is provided with a proximal relay end on a proximal end corresponding to the suction pipe, and an internal diameter of the proximal relay end if not smaller than an internal diameter of the conduit, so that when the proximal relay end and the suction pipe are interconnected with each other, an outer wall of the proximal relay end is embedded with an inner tube wall of the suction pipe;

after the working section of the electrosurgical pencil penetrates into the elastic securing tube until a neck portion of the working section is clamped and locked by the elastic inner wall of the elastic securing tube, the blade portion of the working section just protruded outside the integrating module, and after the conduit is joined to the suction pipe, a position of the suction pipe is on the same side as the electrosurgical pencil.

2. The electrosurgical pencil integrating module as claimed in claim 1, wherein the conduit has a distal relay end located at the distal end of the conduit and at the location where the blade portion is protruded out, and an internal diameter of the distal relay end is not larger than the diameter of the conduit.

3. The electrosurgical pencil integrating module as claimed in claim 1, wherein an exposed length of the blade portion of the working section is between 1 mm and 5 mm.

4. The electrosurgical pencil integrating module as claimed in claim 2, wherein the distal relay end is additionally interconnected with an insulating pipe, which adjusts the exposed length of the blade portion by cutting the insulating pipe.

5. The electrosurgical pencil integrating module as claimed in claim 4, wherein the exposed length of the blade portion is between 1 mm and 5 mm.

6. The electrosurgical pencil integrating module as claimed in claim 4, wherein the insulating pipe is cylindrical and composed of electric and heat-insulating materials.

7. The electrosurgical pencil integrating module as claimed in claim 1, wherein the elastic securing tube and the conduit are integrally formed.

8. An electrosurgical device possessing module, which comprising:
- an electrosurgical pencil, wherein the electrosurgical pencil further comprises:
  - a handheld section, which is in a long cylindrical shape and used to hold the electrosurgical pencil; and
  - a working section, which is connected to a distal end of the handheld section, which is mainly composed of conductive metal, is provided with an insulating layer at a proximal end of the working section and adjacent to the handheld section, the insulating layer is used to cover a portion of the conductive metal of the working section, and at the distal end of the working section is the blade portion extending from the adjacent insulating layer of the working section;
- an integrating module for assembling the electrosurgical pencil, wherein the integrating module further comprises:
  - an elastic securing tube, which is used for docking and accommodating the working section where the electrosurgical pencil is installed in, and the elastic securing tube has an inlet end, and the diameter of the inlet end is larger than the maximal cross-section of the working section, after the working section of the electrosurgical pencil penetrates into the elastic securing tube, until the working section is clamped and locked by an elastic inner wall of the elastic securing tube; and
  - a conduit, wherein the inner portion of the elastic securing tube and the inner portion of the conduit are interconnected, the conduit is provided with a proximal relay end on the proximal end corresponding to a suction pipe, and the internal diameter of the proximal relay end is not smaller than the internal diameter of the conduit; and
- the axis of the elastic securing tube and the axis of the conduit extend to form an included angle greater than 0 degree and less than 20 degrees; when the neck portion of the working section is secured, the blade portion of the working section is just protruded outside the integrating module.

9. The electrosurgical device possessing module as claimed in claim 8, wherein the handheld section is provided with an operation panel, and the operation panel is provided with a plurality of operation buttons to control different functions of the electrosurgical pencil.

10. The electrosurgical device possessing module as claimed in claim 8, wherein the outer surface of the insulating layer has a plurality of outwardly protruding annular bodies.

11. The electrosurgical device possessing module as claimed in claim 8, wherein the blade portion is in a flat shape.

12. The electrosurgical device possessing module as claimed in claim 8, wherein further comprises a suction pipe, which connects to the proximal relay end of the conduit, and the outer tube wall of the proximal relay end is precisely embedded with the inner tube wall of the suction pipe, to form a continuous channel.

13. The electrosurgical device possessing module as claimed in claim 8, wherein the elastic securing tube and the conduit are integrally formed.

14. The electrosurgical device possessing module as claimed in claim 8, wherein the conduit has a distal relay end located at the distal end of the conduit where the blade portion protruded out, and the inner diameter of the distal relay end is not larger than the internal diameter of the conduit.

15. The electrosurgical device possessing this module as claimed in claim 14, wherein the exposed length of the blade portion of the working section is between 1 mm and 5 mm.

16. The electrosurgical device possessing module as claimed in claim 14, wherein the distal relay end is additionally connected with an insulating pipe, and the user can adjust the exposed length of the blade portion by cutting the insulating pipe.

17. The electrosurgical device possessing module as claimed in claim 16, wherein the exposed length of the blade portion of the working section is between 1 mm and 5 mm.

18. The electrosurgical device possessing module as claimed in claim 13, wherein the insulating pipe is cylindrical and composed of electric and heat-insulating materials.

* * * * *